United States Patent [19]

Coval

[11] 4,124,576
[45] Nov. 7, 1978

[54] METHOD OF PRODUCING INTRAVENOUSLY INJECTABLE GAMMA GLOBULIN

[76] Inventor: Myer L. Coval, 6241 Chelton Dr., Oakland, Calif. 94611

[21] Appl. No.: 747,063

[22] Filed: Dec. 3, 1976

[51] Int. Cl.$^2$ .......................... A23J 1/06; A61K 37/06
[52] U.S. Cl. ................................ 260/112 B; 424/101; 424/177
[58] Field of Search .................... 260/112 B; 424/101, 424/177

[56] References Cited

U.S. PATENT DOCUMENTS

| 3,763,135 | 10/1973 | Shanbrom et al. | 260/112 B |
| 3,808,189 | 4/1974 | Breuer | 260/112 B |

FOREIGN PATENT DOCUMENTS 2,357,800  6/1974  Fed. Rep. of Germany.

Primary Examiner—Walter C. Danison
Attorney, Agent, or Firm—Robert G. Slick

[57] ABSTRACT

An improved process is provided for the preparation of a gamma globulin suitable for intravenous administration from the readily available Fraction II or II + III plasma protein paste or from the corresponding fractions originating from placental extracts. The Fraction II or II + III paste is extracted with water at a pH of 4.9 to 6.0 and impurities are fractionally precipitated by addition of polyethylene glycol to 4% of wt./vol. and then 6% vol. ethanol. The desired gamma globulin is then precipitated at a pH 8.0 by addition of polyethylene glycol to 12% wt./vol.

8 Claims, No Drawings

METHOD OF PRODUCING INTRAVENOUSLY INJECTABLE GAMMA GLOBULIN

SUMMARY OF THE INVENTION

This invention relates to gamma globulins. It particularly relates to a gamma globulin preparation suitable for administration by intravenous injection and to processes for the preparation of said gamma globulin.

The Immunoglobulin G fraction of pooled human plasma contains antibodies to many viruses and bacteria. Immunoglobulins are effective in the clinical management of a wide variety of disease states:
1. Prophylaxis and therapy of infections, in persons with genetic and nosocomial antibody deficiency states, especially staphylococci, pneumococci, streptococci and H. influenzae.
2. Prophylaxis, in patients with normal immunoglobulin levels, of viral infections: (hepatitis, polio, measles, rubeola, rabies, herpes and parotitis), the prophylaxis of tetanus, and of Rh-incompatability.
3. Therapy of severe bacterial infections: staphylococci, coli, pseudomonas, pyocyaneaus septicemias, and also for the therapy of some viral infections such as Herpes zoster.

The full clinical potential of immunoglobulin G has not yet been determined for the following reasons: millions of doses have been give intramuscularly, the intravenous preparations are extremely degraded and low doses have been used. The major antibacterial antibodies in human gammaglobulin are against micro organisms which inhabit the upper respiratory tract, the skin and the gastrointestinal tract. The quantity of gammaglobulin needed to overcome an experimental in vivo infection is proportional to the number of infectious organisms in the inoculum. This has been shown for Pseudomonas aeruginosa, E. coli, proteus, and Staphylococcus aureus. The quantity of gammaglobulin needed is also proportional to the specific antibody level in the preparation. With chloramphenicol there is a synergistic action, but with other antibodies there is only an additive effect.

Human immunoglobulins were first isolated on a large scale during the period from 1945 to 1950 at Harvard in F. J. Cohn's laboratory. It was soon observed that intravenous injection of these preparations caused shock reactions in some patients, and it was subsequently established that the anticomplementary activity of IgG preparations is responsible for the shock reactions. This anticomplementary activity is due to IgG aggregates formed during the fractionation.

In view of these shock reactions associated with the intravenous administration of the immunoglobulins, these therapeutically useful substances were administered intramuscularly instead. However, the intramuscular administration of immunoglobulins has many limitations:
a. they are painful;
b. the amount which can be administered is limited;
c. proteolysis at the site of injection decreases the available IgG;
d. maximum blood levels are attained only after three to four days, which is a serious handicap in those cases requiring high blood levels of IgG immediately after injection.

Furthermore, intravenous administration of immunoglobulins has wider clinical application because the full dose of IgG enters the blood stream immediately without being degraded at the site of injection, and significantly higher blood levels can be attained. These considerations have prompted the search for methods to prepare IgG with low anticomplementary activity which is suitable for intravenous use. The methods which have been developed are based on proteolytic or chemical treatment to abolish the anticomplementary properties of the aggregates.

Examples of preparations obtained by these methods are:
1. Pepsin-treated Immunoglobulin. In this preparation the protein is extensively degraded to antibody fragments (5S,F(ab')$_2$). Its usefulness for combatting bacterial infections is limited because it has a short-life (about 30 hours compared with 20 to 30 days for negative IgG). After combining with antigens, the 5S fragments do not fix complement. It has no application in prophylaxis.
2. Plasmin-treated Immunoglobulin. More than 60 percent of this preparation is degraded to fragments (Fab and Fc). The remaining 7S globulin has a normal half-life (three to four weeks), but the antibody spectrum is limited.
3. pH 4-Treated Immunoglobulin. This preparation has a tendency to become anticomplementary during storage. Its compatibility is therefore restricted and high doses cannot be administered. The half-life is slightly reduced (12 to 14 days) and the antibacterial activity is reduced to an unknown degree.
4. $\beta$ - Propiolactone-Treated Immunoglobulin. The molecules are extensively altered, probably forming new antigenic determinants. The half-life is about 10 days. The bacteriolytic activity is reduced.

The four IgG subclasses have different susceptibilities to proteolysis. The pepsin, plasmin and pH 4 (pepsin) preparations accordingly differ markedly from untreated IgG in their subclass distribution.

As noted above, the undesirable anticomplementary activity which is responsible for the shock reaction produced by the intravenous administration of IgG is due to the aggregates present therein, which are formed during the fractionation procedures used in the preparation. The preparations described above are obtained by methods which use procedures to destroy these aggregates after they formed, in most cases by either chemical or enzymatic degradation. However, such degradation procedures also result in some degradation of the IgG with consequent loss of activity, so such preparations as described above are not as active as desired. Little work has been done on developing methods which prevent the formation of aggregates and provide IgG preparations having substantially no anticomplementary activity.

More recently, there has been disclosed in German Offenlegungschrift 2,357,800, published June 6, 1974, a method for the preparation of a gamma globulin suitable for intravenous administration. This procedure, as well as other published procedures for the preparation of gamma globulin, requires as starting material a relatively purefied gamma globulin fraction. However, of greater significance, the gamma globulin obtained by this method still possesses an excessively high anticomplementary activity for intravenous use.

It has also been proposed (U.S. Pat. No. 3,763,135) to prepare a material suitable for intravenous injection from Fraction III but the process of the present invention gives a much larger yield and the product is much lower in anticomplementary material.

There are Food and Drug Administration standards for intramuscular gamma globulin, but not for intravenous gamma globulin. Such standards are needed to distinguish between gamma globulin which causes shock-like reactions when given by the intravenous route to sensitive individuals and gamma globulin which does not elicit such reactions.

During the past fifteen years, it has been established that no clinical symptoms are observed, even in highly sensitive recipients, when the level of anticomplementary activity is sufficiently low. With the unit of the standard Mayer two unit assay (EXPERIMENTAL IMMUNOCHEMISTRY, By E. A. Kabat and M. M. Mayer 2nd Ed., p. 133, Thomas, Springfield, Ill., 1961), the safe level is 0.04 to 0.02 units or less of anticomplementary material per milligram of Immunoglobulin G, and may be somewhat higher than 0.04, but reactions are routinely observed when the level is 0.04 units per milligram. The designation of gamma globulin preparations as suitable for intravenous use, signifying the absence of clinical reactions, is dependent on a specific low level of anticomplementary activity. It is also necessary to preserve the physiological antibody activity and specificity, in order to provide a clinically safe and effective preparation.

The methods of this patent application have been designed to produce a product which retains the properties of the native gamma globulin molecules, and is essentially devoid of aggregates and their anticomplementary activity, thereby rendering the product safe and effective for intravenous use.

It is, accordingly, an object of the present invention to provide a gamma globulin preparation suitable for intravenous injection.

It is another object of the present invention to provide a gamma globulin preparation suitable for intravenous injection, which has substantially no anticomplementary activity in vitro.

It is a further object of the present invention to provide a gamma globulin preparation suitable for intravenous injection, which has a biological half life of about 3 to 4 weeks.

It is still another object of the present invention to provide a gamma globulin preparation suitable for intravenous injection, which has the ability to fix complement when combined with the corresponding antigen and which has an essentially unaltered antibody spectrum compared with the types and levels of gamma globulin antibodies present in the starting plasma pool and in standard gamma globulin obtained by Cohn's classical ethanol fractionation of plasma.

It is still a further object of the present invention to provide a method for preparing a gamma globulin preparation suitable for intravenous administration.

It is still another object of the present invention to provide a method for preparing from readily available blood protein fractions a gamma globulin preparation suitable for intravenous injection.

It is still a further object of the present invention to provide a method for preparing a gamma globulin preparation suitable for intravenous injection, in which method there is substantially no formation of aggregates.

The process of my copending patent application Ser. No. 688,621 filed 5/21/76 yields a product which is extremely low in anticomplementary material and which is suitable for intramuscular injection. The process of the present invention represents an improvement over the process of said application in that the anticomplementary material is brought to an even lower level and, in fact, it is so low that it cannot be measured by normal analytical methods. In accordance with one aspect of the present invention, a freeze-dried product is produced which has a long shelf life and which is easy to reconstitute.

In accordance with one aspect of the process of the present invention, the gamma globulin is obtained from the readily available Fraction II + III of plasma proteins of Cohn et al as described in the J. Am. Chem. Soc. 68, 459–475 (1946). This fraction, which contains nearly all of the immunoglobulins in addition to other proteins is subjected to novel fractionation techniques which prevent the formation of the aggregates that are formed during the fractionation procedures of the prior art and which yield an active gamma globulin substantially devoid of anticomplementary activity and suitable for intravenous administration.

Another useful source of raw material is the Fraction II material which is readily available as immune serum globulin. This material is economical, stable as a freeze-dried powder, or frozen paste and is free of hepatitis virus. It can be processed in the same way as the Fraction II + III material.

Still another useful starting material is a placental extract containing corresponding fractions.

DESCRIPTION OF THE PREFERRED EMBODIMENTS

In this process a paste of the Fraction II or II + III plasma proteins is extracted with water at a pH of from about 4.9 to 6.0, preferably from about 5.1. Pyrogen free water in a volume of about 25 to 45 liters, preferably 30 liters per kilogram of the paste having a protein content of about 25 to 30% is used. Any non-toxic pharmaceutically acceptable organic or inorganic acid, such as acetic, lactic, citric, hydrochloric, sulfuric, and the like may be used to adjust the pH. The water-insoluble material is separated and the filtrate is then subjected to fractional precipitations, first with polyethylene glycol at a concentration of 4, then with ethanol at concentrations of from 4 to 12%, preferably at about 6% and finally with PEG at 12%, the last at a pH of about 8.0. The first two fractional precipitations remove impurities and the final precipitation yields the desired gamma globulin of the present invention. The preferred polyethylene glycol has a molecular weight of about 4,000 to 12,000. Any non-toxic, pharmaceutically acceptable inorganic base can be used to adjust the pH to about 8.0. The process may be carried out at a temperature of from about 0° to 20° C., but lower temperatures in the range of about −6° to 5° are preferred.

The process is described in detail in the examples. These examples are given by way of illustration and are not to be considered as limiting.

EXAMPLE 1

Cohn Fraction II + III paste is suspended in pyrogen-free distilled water at 0°–5° at a concentration of 30 liters per kilo. A range of 20 to 50 may be used. The pH of the suspension is then adjusted to pH 5.1 (range 4.9 to 6.0) with dilute acetic acid (other acids like those mentioned above can be used). The suspension is then filtered or centifuged at 0°–5°, and the precipitate discarded. The filtrate is brought to 4% polyethylene glycol 4000 (PEG 4000) (PEG 6000 and 12,000 can be used at other concentrations). The precipitate formed in one hour is removed as in the preceding step. The filtrate is then brought to 6% in ethanol (range 4 to 12%), with cautious addition at −2° C. (range 0° to −6°). The precipitate is again removed after 1 to 24 hours, preferably 2 hours.

The solution is then made 0.01 M in NaCl and the pH is adjusted to 8.0 (range 7 to 8.2) with sodium hydroxide (1%). The precipitate formed by the addition of ethanol to 25%, or by PEG 4000 to 10-12% preferably 12% is removed by continuous high speed, flow-thru centrifugation. The resulting paste is dissolved in the following solution: heated human albumin, 5 to 25 mg/ml, preferably 5 to 10 mg/ml, sodium acetate 0.025M, glycine 0.15M, mannitol 1 to 2% preferably 2%, all adjusted with acetic acid to pH 5.1. Lactose may be substituted for mannitol.

The resulting solution, containing 5 to 6% IgG can be lyophilized or stored as a liquid below 10° C. If stored as a liquid, the mannitol is omitted from the dissolving solution. The solution can be lyophilized, freeze dried, in the following manner: the pH is adjusted to 6.4 to 6.6 with 1% sodium hydroxide; after dispensing in vials, in the desired amounts, the solution is then rapidly shell-frozen, and lyophilization is conducted according to current procedures, with care to avoid over-heating after the water has been removed. If lyophilized it is then reconstituted to form a 5 to 6% solution of gamma-globulin. The solution is stable frozen or at 10° for at least one year and the freeze-dried powder for at least 2 years.

The resulting purity is at least 97%, with the only detectable impurity albumin. The anticomplementary activity is below 0.02 units per mg gammaglobulin, range 0.00 to 0.010 units. The units are measured by the two-unit assay of Mayer, cited above.

EXAMPLE 2

Cohn Fraction II paste or powder is dissolved as a 1 to 5 percent solution, preferably 2%, in pyrogen free distilled water, and PEG 2% containing 2 mg of human albumin (range 1 to 10), per ml, at 0° to 5° centigrade. The pH is adjusted to 5.1 (range 4.9 to 6.0, preferably 5.0 to 5.8), and the resulting precipitate formed after 1 hour is removed by filtration or by centrifugation. The PEG concentration of the filtrate is raised to 4 percent with a 50% PEG-4000 solution or with dry PEG 4000 powder. The precipitate formed in one hour is removed. Ethanol is then added to 6% with slow addition so the temperature does not rise above 2° C. The precipitate formed is removed after one to 12 hours, preferably 12 hours. The pH is then raised to 8.0 (range 6.8 to 8.1). The resulting precipitate is collected by centrifugation after raising the ethanol to 25% and dissolved under the same conditions as in the first example.

The product contains over 99% gamma globulin, when measured before the addition of albumin in the dissolving solution. There is no detectable inhibition of hemolysis when 50 mg of the gamma globulin per ml, (a 5 percent solution) is assayed in the standard Mayer assay, or below 0.01 units per mg IgG. The final solution contains only the added albumin, which has been previously heated by conventional procedures to remove any hepatitis B virus. No other proteins can be detected by conventional techniques such as cellulose acetate electrophoresis, immuno-electrophoresis, or immunodiffusion.

EXAMPLE 3

Placental gamma globulin isolated by conventional procedures can be treated as in Example 2. Because placental gamma globulin as isolated conventionally contains a few percent of impurities, which are plasma proteins, additional care is taken to remove all insoluble material at each step, particularly floating insoluble material before the pH is adjusted in the first step and at all other steps. The 6% ethanol filtrate is made 0.01M in NaCl as in the first example. The other steps all as in Example 2. The purity of the product is at least 98 percent gamma globulin, when measured (before the addition of the dissolving solution, which contains albumin, 5 to 10 mg/ml), by the same techniques as in Example 2.

The same dissolving solutions are used as in the first example, with mannitol omitted if the product is desired as a solution, and not to be lyophilized.

EXAMPLE 4

Immunoglobulin G paste or Fraction II, or dried Fraction II powder of placental origin can be highly purified and also used to produce a product suitable for intravenous use by:

1. Suspending the paste or powder at 1% concentration (range 0.3 to 5 percent) in water containing two percent polyethylene glycol 4000 (PEG 2000, 6000, 8000 and 12,000 average molecular weight may also be used), and 0.2 percent heated human albumin at 1° C. (range 0° to 5° centigrade). The insoluble floating material is removed by skimming.
2. The pH is then adjusted to 5.1 (range 4.9 to 6.0) with acetic or hydrochloric or citric or other acids. The precipitate is removed at one degree centigrade after one hour, by filtration or centrifugation.
3. The polyethylene glycol 4000 concentration is then raised to four percent. The floating material is again removed. Then the precipitate is removed by filtration or centrifugation.
4. Ethanol is added to six percent (range 2-12%) by slow addition at 0° C. (range −2 to −15).
5. The precipitate and floating material are removed as in the preceding steps.
6. Sodium chloride is added to 0.01 normality (range 0.03 to 0.05).
7. The pH is then raised to 8.0 (range 7 to 8).
8. Alcohol is added to 25% final concentration slowly at −6° C.
9. The precipitate is collected by centrifugation.
10. The precipitation is dissolved to a final concentration of 5 to 6 percent on the basis of determinations with known weights of paste and known volumes of the following solution: 0.5 percent human heated albumin (range 0.3 to 5 percent), sodium acetate (0.0125 or 0.025 N), glycine 0.15 N, pH 5.1 with acetic acid. The pH of the dissolved paste is adjusted to 6.6 with alkali such as 1 percent sodium hydroxide or potassium hydroxide or tris (hydroxymethyl) amino methane.
11. If the solution is to be lyophilized, 2 percent mannitol is added (range 1 to 3 percent).
12. The resulting solution or freeze-dried powder contains no known impurities, and has less than 0.02 units of anticomplementary activity in the two unit complement assay of Mayer.

13. If the precipitate from step G is analyzed it contains more than 98% gammaglobulin.

The gamma globulin of this invention may be readily incorporated into pharmaceutical preparations suitable for intravenous administration. In formulating such preparation, the gamma globulin is dissolved in an aqueous solution buffered between about 5.4 to 6.7 and containing glycine, albumin and a non-ionic surfactant. The pH of the preparation is then adjusted as desired to a pH between 5.4 to 6.7 and the concentration of the gamma globulin in the preparation is adjusted to 5%. Suitable buffers include phosphate and sodium acetate-acetic acid systems.

To prevent or reduce any denaturation at a liquid-air or liquid solid interface of the product in solution, it is advantageous to add a surfactant to the pharmaceutical composition. Suitable surfactants are non-ionic surfactants such as the block copolymers of propylene and ethylene oxides such as Pluronic 68 (poloxamer 188) and partial esters of sorbitol and polyoxethylene oxide of long chain fatty acids such as the Tweens 20, 40, 60, 80 and 85 (polysorbates 20, 40, 60, 80 and 95), water-soluble substances described in the 1973 edition of the Cosmetic, Toiletry and Fragrance Association, Inc. CTFA Cosmetic Ingredient Dictionary, and fluoro surfactants such as Zonyl FSA, FSB, FSC and FSN. These non-ionic surfactants stabilize proteins against surface denaturation and do not contain as part of their structure any chemical groups which may otherwise interact with or denature proteins.

The gamma globulin of the present invention when stored in the pharmaceutical compositions of the present invention has a longer half life than the other gamma globulin preparations now on the market. The gamma globulin of the present invention has proven to be useful for intravenous administration in all instances and for all conditions where the intravenous administration is desired without any of the usual undesirable effects associated with the intravenous administration of gamma globulins.

I claim:

1. A process for preparing a gamma globulin substantially devoid of anticomplementary activity and suitable for intravenous administration, from a material selected from the Fraction II + III plasma protein paste having a protein content of about 25–30%, Fraction II paste and placental extracts containing these fractions which comprises the steps:

a. suspending said paste in water to form a solution of low ionic strength having a conductance of about $300 \times 10^{-6} cm^{-1} ohm^{-1}$ at a pH of about 4.9 to 6.0 to produce a precipitate and a filtrate,
    b. precipitating impurities from said filtrate by adding polyethylene glycol to 4% weight/volume,
    c. further precipitating impurities by the addition of ethanol in a concentration of from 4 to 12% and
    d. precipitating the gamma globulin by adding polyethylene glycol to 10 to 12% weight/volume or by adding ethanol to 20 to 30% v/v, preferably 25% at a pH of from 7 to 8.2, preferably 8.0.

said process being carried out at a temperature of about 0° to −6° C.

2. A process according to claim 1 wherein the pH at which the paste is extracted is about 5.1.

3. A process according to claim 1 wherein the polyethylene glycol has a molecular weight of about 4,000 to 6,000.

4. A process according to claim 4 wherein the polyethylene glycol has a molecular weight of about 4,000.

5. A process according to claim 4 wherein the process is carried out at a temperature of about −2.

6. A lyophilized gamma globulin prepared by the method of claim 1 suitable for intravenous administration which has from zero to about 0.02 units per mg. of anticomplementary activity, a sedimentation coefficient of 7S, contains no aggregates and degradation products $F(ab)_1$, $F(ab)_2$ or Fc, readily dissolves in water to give clear and colorless solutions, and whose antibody spectrum levels and sublcass distribution are unaltered from that of the starting material.

7. The process of claim 1 wherein the starting material is a placental extract and the solutions of steps a, b and c are subjected to a skimming operation.

8. The process of claim 1 wherein the initial suspension is made in water containing about 2% polyethylene glycol and about 0.2% albumin.

* * * * *